United States Patent [19]

Wechter et al.

[11] 3,953,468
[45] Apr. 27, 1976

[54] 3-CYANO THIOPHEN-2-YL OXAMIC ACID AND DERIVATIVES

[75] Inventors: William J. Wechter; John B. Wright, both of Kalamazoo, Mich.

[73] Assignee: The Upjohn Company, Kalamazoo, Mich.

[22] Filed: Mar. 15, 1974

[21] Appl. No.: 451,509

[52] U.S. Cl. .................. 260/332.2 R; 260/294.8 C; 260/329 AM; 424/263; 424/275; 260/268 H
[51] Int. Cl.² ........................................ C07D 333/24
[58] Field of Search .............. 260/329 AM, 332.2 R, 260/332.2 A

[56] References Cited
UNITED STATES PATENTS 3,705,910   12/1972   Lundberg et al. ............... 260/332.2

*Primary Examiner*—Bernard Helfin
*Assistant Examiner*—A. Siegel
*Attorney, Agent, or Firm*—Martin B. Barancik; Roman Saliwanchik

[57] ABSTRACT

Compounds represented below

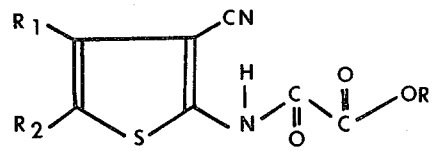

and pharmaceutical compositions thereof are useful in the prophylactic treatment of mammals for allergy and all anaphylactic reactions of a reagin or non-reagin mediated nature.

8 Claims, No Drawings

3-CYANO THIOPHEN-2-YL OXAMIC ACID AND DERIVATIVES

BRIEF SUMMARY OF THE INVENTION

It has now been discovered that novel compounds of Figure I are useful in the prophylactic treatment of sensitized humans and animals for allergy and all anaphylactic reactions of a reagin or non-reagin mediated nature. The compounds are formulated with pharmaceutical carriers for oral, parenteral, inhalation and rectal means of administration.

DETAILED DESCRIPTION OF THE INVENTION

In accordance with this invention, there are provided compounds represented by Figure I and hereafter referred to as Group A:

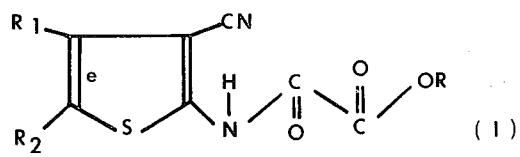

wherein R is selected from the group consisting of hydrogen, alkyl from one to ten carbon atoms, inclusive, phenyl, benzyl, and a pharmaceutically acceptable metal or amine cation; $R_1$ and $R_2$ are the same or different and are selected from the group consisting of hydrogen, alkyl of one to six carbon atoms, inclusive, phenyl, with the proviso that $R_2$ can be O-alkyl where alkyl is one to six carbon atoms, inclusive, and $R_1$ and $R_2$ when joined with the carbon atoms to which they are attached, e denoting the common double bond of the thiophene ring and the ring formed when $R_1$ and $R_2$ are joined with the carbon atoms to which they are attached, form the following groups:

a.

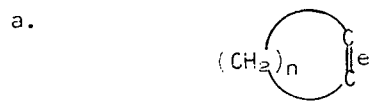

where $n$ is an integer from three to ten, inclusive;

b.

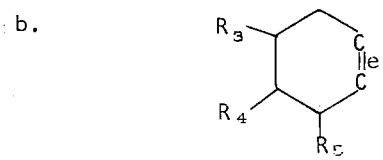

where $R_3$, $R_4$ and $R_5$ are the same or different and are selected from the group consisting of hydrogen and alkyl from one to four carbon atoms, inclusive;

c.

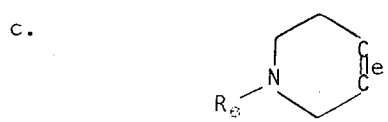

where $R_6$ is selected from the group consisting of hydrogen, alkyl from one to four carbon atoms, inclusive, phenyl, and benzyl;

d.

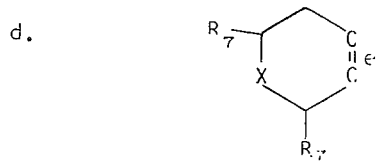

wherein X is selected from the group consisting of sulfur and $NR_8$ where $R_8$ is selected from the group consisting of hydrogen and alkyl of one to three carbon atoms and $R_7$ is selected from the group consisting of phenyl and mono or di-halogenated or trifluoromethylated phenyl;

and

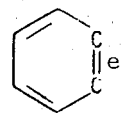

A further group of compounds of the invention, hereafter referred to as Group B, are compounds of Figure I wherein R is defined as in Group A and $R_1$ and $R_2$ are the same or different and are selected from the group consisting of hydrogen, alkyl of one to four carbon atoms, inclusive, phenyl, with the proviso that $R_2$ can be O-alkyl with alkyl of one to three carbon atoms, inclusive, and $R_1$ and $R_2$, when joined together with the carbon atoms to which they are attached, form the following groups, e defined as in Group A:

a.

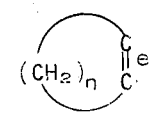

where $n$ is an integer from three to ten, inclusive;

b.

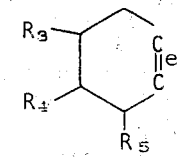

where $R_3$, $R_4$ and $R_5$ are the same or different and are selected from the group consisting of hydrogen and methyl, c.

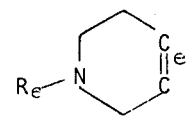

where $R_6$ is selected from the group consisting of methyl, n-butyl and benzyl, d.

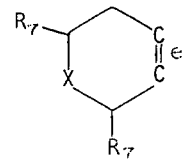

wherein X is sulfur or N-methyl and $R_7$ is phenyl; and

A still further group of compounds of the invention, hereafter referred to as Group C, are compounds of Figure I wherein R is hydrogen, alkyl of one to three carbon atoms inclusive, and a pharmaceutically acceptable metal or amine cation, $R_1$ and $R_2$ are the same or different and are selected from the group consisting of hydrogen, alkyl of one to four carbon atoms, inclusive, phenyl, and with the proviso that $R_2$ is O-alkyl with alkyl of one to three carbon atoms, inclusive, and $R_1$ and $R_2$, when joined together with the carbon atoms to which they are attached, form the following groups, e defined as in Group A:

a.
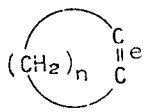

where $n$ is an integer of three to six, inclusive;

b.
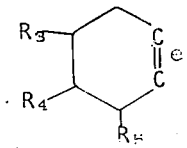

where $R_3$, $R_4$, and $R_5$ are the same or different and are selected from the group consisting of hydrogen and methyl, and

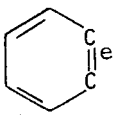

Another group of compounds, hereafter referred to as Group D, are compounds of Figure I wherein R is selected from the group consisting of hydrogen and a pharmaceutically acceptable metal or amine cation; $R_1$ and $R_2$ are the same or different and are selected from the group consisting of alkyl of one to four carbon atoms, inclusive, and phenyl, and when $R_1$ and $R_2$ are joined with the carbon atoms to which they are attached, e defined as in Group A, form:

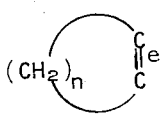

wherein $n$ is an integer of three to six, inclusive, and

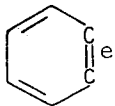

Preferred compounds are (3-cyano-4,5-dimethylthiophene-2-yl)oxamic acid and (3-cyano-4,5-tetramethylenethiophene-2-yl)oxamic acid, esters and salts thereof, particularly the tris(hydroxymethyl)aminomethane salt.

As employed in the above disclosure and throughout the specification, the term "halogen" means fluoro, chloro, bromo, and iodo. The term "alkyl" includes methyl, ethyl, propyl and isopropyl when limited to three carbon atoms; and butyl and isomers thereof when limited to four carbon atoms; and pentyl; hexyl and isomers thereof when limited to six carbon atoms; and heptyl, octyl, nonyl, decyl and isomers thereof when limited to ten carbon atoms. The term "pharmaceutically acceptable metal" includes alkali metals such as sodium and potassium, alkaline earth metals such as calcium and magnesium and other acceptable metals such as aluminum. The term "amine cation" includes all pharmaceutically acceptable cations from amines, such as ammonia, tris(hydroxymethyl)aminomethane, D-threo-2-amino-1-p-nitrophenyl-1,3-propanediol, N,N-bis(hydroxyethyl)piperazine, 2-amino-2-methyl-1-propanol, 2-amino-2-methyl-1,3-propanediol and 2,2-bis(hydroxymethyl)-2,2',2''-nitrilotriethanol and further amines including $H_2NR'$, $HNR'_2$, and $NR'_3$, wherein $R'$ is selected from the group consisting of alkyl from one to three carbon atoms, inclusive, and $-CH_2CH_2OH$.

The compounds of this invention can be prepared by methods known to the art. An $R_1$ and $R_2$ substituted 2-amino-3-cyano-thiophene (II) is a suitable starting material. This compound is reacted with an alkyl oxalyl halide, alkyl having one to three carbon atoms, inclusive, preferably ethyl oxalyl chloride (IIIa) in a suitable solvent and base to form the oxamate (IV). An alternative method of preparing the oxamate is to react (II) with a dialkyl oxalate, alkyl having one to three carbon atoms, inclusive, preferably diethyl oxalate (IIIb) in neat or with an additional solvent if necessary at a temperature ranging from about 100° to about reflux temperature of the system

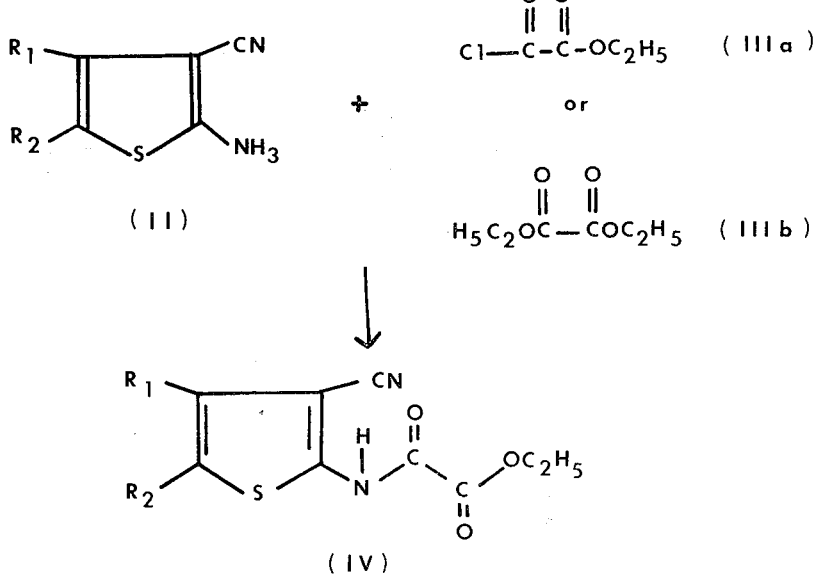

At this point of the synthetic pathway, the oxamate can be transesterified to other esters and/or converted to the acid by hydrolysis and thence to the metal or amine salts by standard methods.

The $R_1$ and $R_2$ substituted 2-amino-3-cyanothiophene compounds are prepared by the methods of Gewald, et al., Chem. Ber. 99, 94, 1966; Rosowsky et al., J. Med. Chem., 16, No. 3, 185 and Chaykovsky et al., J. Med. Chem. 16, No. 3, 188. The Gewald reference addresses itself essentially to the direct one-step base-catalyzed condensation of ketones with malononitrile and sulfur. The other articles expanded the work of Gewald and co-workers.

Once starting material II is prepared, it is reacted with an alkyl oxalyl halide or dialkyl oxalate. When using an alkyl oxalyl halide, reaction is carried out in base and solvent at standard conditions. Examples of suitable solvents are dimethylformamide, ethyl acetate, dioxane, and tetrahydrofuran. Appropriate bases include triethylamine, N-methylmorpholine, dimethylpiperazine, and N-methylpiperidine. When the dialkyl oxalate is employed, the starting material II or its substituted analogue is heated together with the dialkyl oxalate or an additional solvent such as a xylene or diphenyl ether if desired, thereby forming the oxamate. The temperature is from about 100°C. to the reflux temperature of the system.

The oxamate is then readily converted to the oxamic acid by using dilute base such as sodium hydroxide, potassium hydroxide or potassium carbonate at temperatures ranging from about 25° to about 100°C., followed by addition of acid. The alkaline metal salts of the oxamate may be soluble in aqueous medium or relatively insoluble. If soluble in aqueous medium, the pH is adjusted with acid and the resulting precipitate is collected. If the alkaline metal salt is insoluble in aqueous medium, the precipitate per se can be collected and then heated in aqueous acid to an appropriate temperature, collecting the mixture and isolating the desired acid. The acid can then be easily converted to the metal or amine salt by contacting the acid with an equivalent of the desired amine or metal and heating in a sufficient amount of water to effect solubilization. The crystalline salts can be precipitated by the addition of an organic solvent, for example, methanol.

As an illustration, the tris(hydroxymethyl)aminomethane (THAM) salt of the acids of Figure I can be prepared, according to the art, by dissolving the carboxylic acid in an aqueous solution containing an equivalent weight of THAM base. The resulting solution of the THAM salt may be used directly, or the salt may be obtained dry by precipitation or evaporation, according to the art.

Following is an illustrative list of compounds of the invention which can be prepared by the above disclosed procedures:

TABLE I

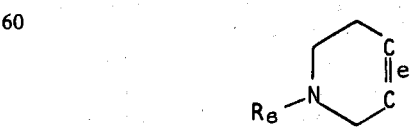

| $R_1$ | $R_2$ |
|---|---|
| H | H |
| $CH_3$ | H |
| H | $C_6H_{13}$ |
| $iC_6H_{13}$ | H |
| $C_2H_5$ | $tC_5H_{11}$ |
| $C_3H_7$ | $iC_4H_9$ |
| $iC_3H_7$ | $iC_3H_7$ |
| H | $C_6H_5$ |
| $C_6H_5$ | H |
| $C_6H_5$ | $C_6H_5$ |
| $C_6H_5$ | $CH_3$ |
| $C_2H_5$ | $C_6H_5$ |
| $C_6H_5$ | $iC_3H_7$ |
| $tC_4H_9$ | $C_6H_5$ |
| $C_6H_5$ | $C_5H_{11}$ |
| $iC_6H_{13}$ | $C_6H_5$ |
| H | $OCH_3$ |
| $CH_3$ | $OC_2H_5$ |
| $C_2H_5$ | $OC_3H_7$ |
| $C_4H_9$ | $OiC_4H_9$ |
| $iC_5H_{11}$ | $OC_5H_{11}$ |
| $C_6H_{13}$ | $OiC_6H_{13}$ |
| $C_6H_5$ | $OC_2H_5$ |

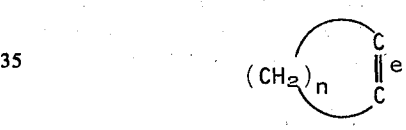

$n = 3, 4, 5, 6, 7, 8, 9, 10$

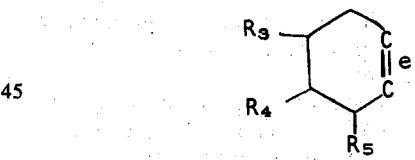

| $R_3$ | $R_4$ | $R_5$ |
|---|---|---|
| H | H | $CH_3$ |
| H | $CH_3$ | H |
| $CH_3$ | H | H |
| $C_2H_5$ | $C_2H_5$ | $C_2H_5$ |
| $C_3H_7$ | H | $CH_3$ |
| $iC_3H_7$ | $C_2H_5$ | H |
| H | $C_4H_9$ | $CH_3$ |
| $iC_4H_9$ | $C_2H_5$ | H |
| $C_2H_5$ | $tC_4H_9$ | $CH_3$ |

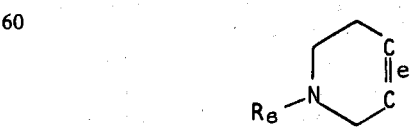

| $R_6$ |
|---|
| H |
| $CH_3$ |
| $C_2H_5$ |
| $C_3H_7$ |

-continued

| R₈ |
|---|
| iC₃H₇ |
| C₄H₉ |
| iC₄H₉ |
| tC₄H₉ |
| C₆H₅ |
| C₆H₅CH₂ |

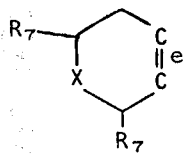

| X | R₇ |
|---|---|
| S | C₆H₅ |
| S | 2-ClC₆H₄ |
| S | 3,4-diClC₆H₃ |
| S | 4,6-diClC₆H₃ |
| S | 4-CF₃C₆H₄ |
| S | 3,5-diCF₃C₆H₃ |
| N-H | C₆H₅ |
| N-CH₃ | 2-ClC₆H₄ |
| N-C₂H₅ | 3,4-diClC₆H₃ |
| N-C₃H₇ | 4-CF₃C₆H₄ |
| N-iC₃H₇ | C₆H₅ |

TABLE II

The compounds of Table I are converted to pharmaceutically acceptable salts, particularly tris(hydroxymethyl)methylammonium by standard methods.

TABLE III

The compounds of Table I are prepared where R is alkyl of one to ten carbon atoms, inclusive, phenyl and benzyl.

Tables II and III are not rendered in the same manner as Table I for the purpose of brevity. However, the same scoping is intended.

The following examples are compounds in accordance with this invention. The compounds are intended not to limit but merely to exemplify the invention.

EXAMPLE 1

Sodium (3-cyano-4,5-tetramethylenthiophen-2-yl)oxamate a. (2-Amino-3-cyano-4,5-tetramethylenthiophen)

This compound is prepared according to the procedure of K. Gewald, et al., Chem. Ber. 99, 94 (1966).

b. Ethyl (3-cyano-4,5-tetramethylenthiophen-2-yl)oxamate 5.31 g. of 2-amino-3-cyano-4,5-tetramethylene thiophene (0.03 mole) is dissolved in 50 ml. of ethyl acetate containing 3.12 g. (0.031 mole) of triethylamine. Ethyl oxalylchloride (4.2 g., 0.0308 mole) in 25 ml. of ethyl acetate is added dropwise at 5°C. during twenty minutes. The reaction mixture is warmed to room temperature with stirring overnight. The triethylamine hydrochloride is removed by filtration, and the filtrate concentrated in vacuo to yield about 8.9 g. of solid. The solid is recrystallized from 50 ml. of absolute ethanol to yield 4.76 g. of granular crystals melting at 102.5°–104°. This solid is further purified by silica gel chromatography to yield a large central fraction (2.31 g.) melting at 110°–111°. A sample crystallized from ethanol melts at 110°–111° and analyzes correctly for ethyl (3-cyano-4,5-tetramethylenthiophen-2-yl)oxamate.

Anal. Calcd. for: $C_{13}H_{14}O_3N_2S$ C, 56.10; H, 5.07; N, 10.7; S, 11.52 Found: C, 55.88; H, 5.22; N, 10.20; S, 11.26 c. Sodium (3-cyano-4,5-tetramethylenthiophen-2-yl)oxamate

Approximately 0.91 g. of ethyl (3-cyano-4,5-tetramethylenthiophen-2-yl)oxamate (0.00328 mole) is hydrolyzed to the sodium salt by the addition of 33.0 ml. of 0.10N NaOH solution. The ester is completely hydrolyzed after 2 hours and the solution concentrated in vacuo to recover the sodium salt of (3-cyano-4,5-tetramethylenthiophen-2-yl)oxamic acid. If desired the sodium salt is recovered in part by concentrating to about 25 ml., filtering the solid and washing with EtOH. The salt is a high melting solid which chars.

EXAMPLE 2

Sodium (3-cyano-4,5-dimethylthiophen-2-yl)oxamate a. 2-Amino-3-cyano-4,5-dimethylthiophene This compound is synthesized by the procedure of K. Gewald, et al., Chem. Ber., 99, 94 (1966).

b. Ethyl (3-cyano-4,5-dimethylthiophen-2-yl)-oxamate

From 7.61 g. of 2-amino-3-cyano-4,5-dimethylthiophene (0.05 mole), 5.06 g. (0.05 mole) of triethylamine, 6.83 g. (0.05 mole) of ethyl oxalylchloride in about 125 ml. of ethyl acetate, the procedure used in Example 1-b above yields 13.0 g. of crude ethyl (3-cyano-4,5-dimethylthiophen-2-yl)oxamate (M.P. is 84°–90°). About 5 g. of this crude product is crystallized from 40 ml. of absolute ethanol to yield 2.79 g. of purified ester melting at 94°–95°.

c. Sodium (3-cyano-4,5-dimethylthiophen-2-yl)oxamate

Approximately 0.756 g. (0.003 mole) of the purified ethyl (3-cyano-4,5-dimethylthiophen-2-yl)oxamate is suspended in 20 ml. of water and hydrolyzed by the addition of 32 ml. of 0.1N NaOH in a dropwise manner during about twenty minutes. The hydrolysis mixture is stirred for an additional twenty minutes at room temperature. The clear yellow solution (pH 9.2) is adjusted to pH 8.3 with 2 ml. of 0.1N HCl and concentrated in vacuo to recover the sodium salt of (3-cyano-4,5-dimethylthiophen-2-yl)oxamic acid as a yellow solid.

The compositions of the present invention are presented for administration to humans and animals in unit dosage form, such as tablets, capsules, pills, powders, granules, sterile parenteral solutions or suspensions, eye drops, oral solutions or suspensions, oil-in-water and water-in-oil emulsions and suppositories containing suitable quantities of the compound of Formula I. The preferred method of administration is by inhalation into the lung by means of an aerosol liquid or powder for insufflation.

For oral administration, either solid or fluid unit dosage forms can be prepared. For preparing solid compositions such as tablets, the compound of Figure I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (e.g., ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 g.

The preferred compositions are those adapted for inhalation into the lung and containing a compound of the invention which is water-soluble. For treatment of allergic conditions of the nose, such as rhinitis, compositions adapted for contact with nasal linings are preferred.

Compositions for inhalation are of three basic types: 1) a powder mixture preferably micropulverized with particle size preferably from about 1 to about 5 microns; 2) an aqueous solution to be sprayed with a nebulizer; and 3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when insufflated through the mouth.

Aqueous solutions are prepared by dissolving the compound of Figure I in water and adding salt to provide an isotonic solution and buffering to a pH compatible with inhalation. The solutions are dispersed in a spray device or nebulizer and sprayed into the mouth while inhaling.

Aerosols are prepared by dissolving a compound of the Figure I in water or ethanol and mixing with a volatile propellant and placing in a pressurized container having a metering valve to release a predetermined amount of material.

The liquefied propellant employed is one which has a boiling point below 65°F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl, chlorides. Further suitable liquefied propellants are the fluorinated and fluorochlorinated lower alkanes such as are sold under the trademarks "Freon" and "Genetron". Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane ("Freon 13").

The term "unit dosage form" as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampuls, vials, aerosols with metered discharges, segregated multiples of any of the foregoing, and other forms as herein described.

An effective but non-toxic quantity of the compound is employed in treatment. The dosage of the compound for treatment depends on the route of administration and the potency of the particular compound. A dosage schedule for humans of from about 0.02 to about 200 mg. of compound in a single dose, administered parenterally or by inhalation in the compositions of this invention, are effective for preventing allergy attacks.

More specifically, the single dose is from about 1 to about 200 mg. of compound. The oral and rectal dose is from about 10 to about 200 mg. in a single dose. More specifically, the single dose is from about 20 to about 200 mg. of compound. The dosage to be administered can be repeated up to four times daily. However, when it is necessary to repeat treatment, a preferred dosage schedule reduces the secondary treatment dosage to from about 0.5 percent to about 20 percent of the above dosages, more specifically, from about 1 to about 10 percent of the above dosages. In this manner, a state of allergy prophylaxis can be maintained. The reduced dosage is taken until that dosage no longer provides effective protection. At that time, the larger dosage is repeated, followed by the reduced dosage. An example of such a dosage schedule is the following: An asthmatic individual insufflates 4 mg. of sodium (3-cyano-4,5-tetramethylenthiophen-2-yl)oxamate. Four hours later the individual insufflates 0.1 mg. of the same compound and every four to six hours thereafter insufflates 0.1 mg. of the same compound until effective asthma prophylaxis is not provided. The individual then insufflates 4 mg. of the same compound, then reduces the insufflation dosage to 0.1 mg. 4 to 6 hours later. The dosage schedule continues in this manner.

The administration of the compositions of the present invention to humans and animals provides a method for the prophylactic treatment of allergy or all anaphylactic reactions of a reagin or non-reagin mediated nature. That is to say, these compositions, when administered to a sensitized individual prior to the time that the individual comes into contact with substances antigens) to which he is allergic, will prevent the allergic reaction which would otherwise occur.

For example, the process can be used for prophylactic treatment of such chronic conditions as bronchial asthma, allergic rhinitis, food allergy, hay fever, urticaria, auto-immune diseases, exercise induced asthma, stress induced asthma, systemic anaphylaxis, and bird fancier's disease.

EXAMPLE 3

A lot of 10,000 tablets, each containing 10 mg. of (3-cyano-4,5-tetramethylenthiophen-2-yl)oxamic acid is prepared from the following types and amounts of ingredients:

| | |
|---|---|
| (3-cyano-4,5-tetramethylenthiophen-2-yl)oxamic acid | 100 Gm. |
| Dicalcium phosphate | 1000 Gm. |
| Methylcellulose, U.S.P. (15 cps) | 60 Gm. |
| Lactose | 150 Gm. |
| Corn starch | 200 Gm. |
| Magnesium stearate | 10 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever attack at a dose of 1 tablet every 4 to 6 hours.

EXAMPLE 4

One thousand two-piece hard gelatin capsules, each containing 5 mg. of sodium (3-cyano-4,5-tetramethylenthiophen-2-yl)oxamate are prepared from the following types and amounts of ingredients:

| | |
|---|---|
| Sodium (3-cyano-4,5-tetramethylenthiophen-2-yl)oxamate | 5 Gm. |
| Lactose | 150 Gm. |
| Magnesium stearate | 1 Gm. |

The ingredients are mixed well and filled into capsules of the proper size.

Capsules so prepared are useful in preventing attacks of bronchial asthma at a dose of one capsule every 4 to 6 hours.

EXAMPLE 5

One thousand tablets, each containing 5 mg. of sodium (3-cyano-4,5-tetramethylenthiophen-2-yl)oxamate are prepared from the following types and amounts of ingredients:

| | |
|---|---|
| Sodium (3-cyano-4,5-tetramethylenthiophen-2-yl)oxamate | 5 Gm. |
| Microcrystalline cellulose NF | 410 Gm. |
| Starch | 100 Gm. |
| Magnesium stearate powder | 3 Gm. |

The ingredients are screened and blended together and pressed into tablets.

The tablets are useful to protect against food allergy at a dose of 1 tablet before meals.

EXAMPLE 6

A sterile preparation suitable for intramuscular injection and containing 4 mg. of sodium (3-cyano-4,5-tetramethylenthiophen-2-yl)oxamate in each milliliter is prepared from the following ingredients:

| | |
|---|---|
| Sodium (3-cyano-4,5-tetramethylenthiophen-2-yl)oxamate | 4 Gm. |
| Benzyl benzoate | 200 ml. |
| Methylparaben | 1.5 Gm. |
| Propylparaben | 0.5 Gm. |
| Cottonseed oil q.s. | 1000 ml. |

One milliliter of this sterile preparation is injected for prophylactic treatment of allergic rhinitis.

EXAMPLE 7

Six hundred ml. of an aqueous solution containing 10 mg. of sodium (3-cyano-4,5-tetramethylenthiophen-2-yl)-oxamate per ml. is prepared as follows:

| | |
|---|---|
| Sodium (3-cyano-4,5-tetramethylenthiophen-2-yl)oxamate | 6 Gm. |
| Sodium chloride | 5 Gm. |
| Water for injection q.s. | 600 ml. |

The sodium salt and sodium chloride are dissolved in sufficient water to make 600 ml. and sterile filtered.

The solution is placed in nebulizer designed to deliver 1.0 ml. of solution per spray.

The solution is inhaled into the lungs every 4 to 6 hours for prevention of asthmatic attacks.

EXAMPLE 8

A powder mixture consisting of 0.10 gram of sodium (3-cyano-4,5-tetramethylenthiophen-2-yl)oxamate and sufficient lactose to make 5 grams of mixture is micropulverized and placed in an insufflator designed to deliver 50 mg. of powder per dose.

The powder is inhaled into the lungs every 4 to 6 hours for prevention of asthmatic attacks.

The powder is inhaled intranasally every 4 hours for prevention of rhinitis.

EXAMPLE 9

A powder mixture consisting of 0.004 gram of sodium (3-cyano-4,5-tetramethylenthiophen-2-yl)oxamate and sufficient lactose to make 5 grams of mixture is micropulverized and placed in an insufflator designed to deliver 50 mg. of powder per dose.

The powder is inhaled into the lungs every 4 to 6 hours for prevention of asthmatic attacks, following a prior inhalation of the powder of Example 8.

EXAMPLE 10

Twelve grams of an aerosol composition are prepared from the following ingredients:

| | |
|---|---|
| Tris(hydroxymethyl)aminomethane salt of (3-cyano-4,5-tetramethylenthiophen-2-yl)-oxamic acid | 0.05 Gm. |
| Freon 12 | 1.44 Gm. |
| Freon 114 | 2.16 Gm. |
| Water | 7.75 Gm. |
| Sorbitan monoleate | 0.60 Gm. |

The THAM salt is dissolved in the water and chilled to −30°C. and added to the chilled Freons. The twelve grams of compositions are added to a 13 cc. plastic coated bottle and capped with a metering valve. The metering valve releases 80 mg. of composition in an aerosol. The aerosol is inhaled every 4 to 6 hours for prevention of asthmatic attacks.

EXAMPLE 11

In individuals who require continual treatment in the Examples 3 through 8 and 10, the dosage of the Example is given initially and each succeeding administration of the drug is at 1/50 of the initial dosage. This maintenance dosing is continued until effective allergy prophylaxis is not obtained. The initial dosage of Examples 3 through 8 and 10 is then started once more, followed by the maintenance dosages.

EXAMPLE 12

After allowing for the differing solubilities of the compounds and the activity of the particular compound as measured, for example, by the in vivo rat passive cutaneous anaphylaxis assay, a suitable quantity of each of the compounds of Table I through Table III and Examples 1-2, is substituted for the active compound in the compositions and uses of Examples 3 through 11. Results showing anti-allergy activity are obtained.

EXAMPLE 13

The rat passive cutaneous anaphylaxis assay is run in the following manner:

Female Sprague-Dawley 250 gm. rats are skin-sensitized with rat anti-ovalbumin homocytotropic antibody that is heat labile and has a passive cutaneous anaphylaxis titer of 1:128. After a 72-hour latency period, the animals are challenged i.v. with 4 mg. ovalbumin (OA) + 5 mg. Evans blue dye and the test compound. Thirty minutes later the extravascular bluing that results from antigen antibody combination at the skin site is read. Antibody dilutions are used such that in control animals a 4 mm spot is the lowest detectable spot, and 4 or 5 lower dilutions are used to give a range of antibody in each animal. Four to five animals are used for each variable in the experiment. Percent inhibition of the PCA assay is calculated by comparing the spot scores of treated rats with the spot scores of control rats. The spot score is the total number of detectable spots divided by the number of animals.

The inhibitory dose$_{50}$ for the sodium salt of (3-cyano-4,5-tetramethylene-2-yl)oxamic acid is 0.1 mg./kg. by the intravenous route.

Additional pharmaceutically acceptable amine cations include cations from heterocyclic amines such as piperidine, morpholine, pyrrolidine, piperazine, and lower alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and quaternary amines, for example, tetramethylammonium, tetraethylammonium, benzyltrimethylammonium, phenyltriethylammonium and the like.

We claim:
1. A compound of the formula

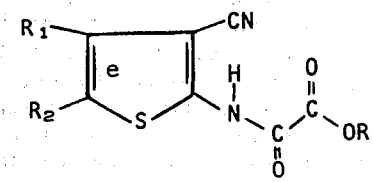

wherein R is selected from the group consisting of hydrogen, alkyl from one to ten carbon atoms, inclusive, phenyl, benzyl, and a pharmaceutically acceptable metal or amine cation; $R_1$ and $R_2$ are the same or different and are selected from the group consisting of hydrogen, alkyl of one to six carbon atoms, inclusive, phenyl, and $R_1$ and $R_2$, when joined with the carbon atoms to which they are attached, e denoting the common double bond of the thiophene ring and the ring formed when $R_1$ and $R_2$ are joined together with the carbon atom to which they are attached, form the following groups:

a.

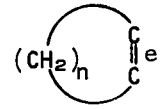

where $n$ is an integer from three to ten, inclusive;

b.

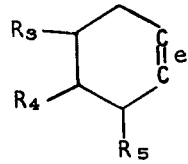

where $R_3$, $R_4$, and $R_5$ are the same or different and are selected from the group consisting of hydrogen and alkyl from one to four carbon atoms, inclusive; with the proviso that $R_3$, $R_4$, and $R_5$ are each not hydrogen at the same time.

2. Compounds in accordance with claim 1 wherein $R_1$ and $R_2$ are the same or different and are selected from the group consisting of hydrogen, alkyl of one to four carbon atoms, inclusive, phenyl, alkoxy with alkyl of one to three carbon atoms, inclusive, and $R_1$ and $R_2$, when joined together with the carbon atoms to which they are attached, e defined as in claim 1, form the following groups:

a.

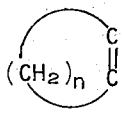

where *n* is an integer from three to ten, inclusive;

b.

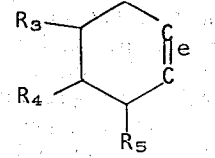

where $R_3$, $R_4$, and $R_5$ are the same or different and are selected from the group consisting of hydrogen and methyl, with the proviso that $R_3$, $R_4$, and $R_5$ are each not hydrogen at the same time.

3. Compounds in accordance with claim 2 wherein R is hydrogen, alkyl of one to three carbon atoms, inclusive, and a pharmaceutically acceptable metal or amine cation, $R_1$ and $R_2$ are the same or different and are selected from the group consisting of hydrogen, alkyl of one to four carbon atoms, inclusive, phenyl and and $R_1$ and $R_2$, when joined together with the carbon atoms to which they are attached, *e* defined as in claim 1, form the following groups:

a.

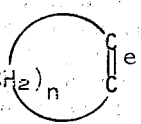

where *n* is an integer of three to six, inclusive;

b.

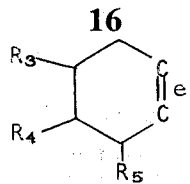

where $R_3$, $R_4$ and $R_5$ are the same or different and are selected from the group consisting of hydrogen and methyl, with the proviso that $R_3$, $R_4$, and $R_5$ are each not hydrogen at the same time.

4. Compounds in accordance with claim 3 wherein R is selected from the group consisting of hydrogen and a pharmaceutically acceptable metal or amine cation; $R_1$ and $R_2$ are the same or different and are selected from the group consisting of alkyl of one to four carbon atoms, inclusive, and phenyl, and when $R_1$ and $R_2$ are joined with the carbon atoms to which they are attached, *e* defined as in claim 1, form wherein *n* is an integer of three to six, inclusive.

5. (3-Cyano-4,5-dimethylthiophen-2-yl)oxamic acid, alkyl esters thereof having one to ten carbon atoms, inclusive, phenyl ester thereof, and pharmaceutically acceptable metal or amine salts thereof according to claim 1.

6. (3-Cyano-4,5-dimethylthiophen-2-yl)oxamic acid according to claim 1.

7. (3-Cyano-4,5-tetramethylene-thiophene-2-yl)oxamic acid, alkyl esters thereof having one to ten carbon atoms, inclusive, phenyl ester thereof, and pharmaceutically acceptable metal or amine salts thereof according to claim 1.

8. (3-Cyano-4,5-tetramethylene-thiophene-2-yl)oxamic acid according to claim 1.

* * * * *

UNITED STATES PATENT OFFICE
CERTIFICATE OF CORRECTION

Patent No. 3,953,468                    Dated April 27, 1976

Inventor(s) William J. Wechter and John B. Wright

It is certified that error appears in the above-identified patent and that said Letters Patent are hereby corrected as shown below:

Column 2, last formula, " 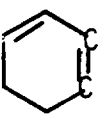 e" should read -- 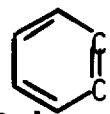 e -- ;
Column 3, line 4, "atoms" should read --atoms,--; Column 4, line 17, "pentyl;" should read --pentyl,--; formula (II), "NH₃" should read --NH₂--; Column 6, line 25, "         " should read --_____--; Column 8, line 9, "10.7" should read --10.07--; Column 12, line 56, "nebulizer" should read --nebulizers--; Column 14, lines 14-15, "2methylpyrrolidine," should read -- 2-methylpyrrolidine,--; lines 65-66, "phenyl, alkoxy with alkyl of one to three carbon atoms, inclusive, and R₁" should read --phenyl, and R₁--; Column 15, line 26, claim 3, "phenyl and and R₁" should read --phenyl and R₁-- .

Signed and Sealed this

Third Day of April 1979

[SEAL]

Attest:

RUTH C. MASON
Attesting Officer

DONALD W. BANNER
Commissioner of Patents and Trademarks